United States Patent
Crimi et al.

(10) Patent No.: US 8,945,594 B2
(45) Date of Patent: Feb. 3, 2015

(54) VINYLIC MASK WITH PEEL-OFF EFFECT FOR TOPICAL USE CONTAINING HIGH CONCENTRATIONS OF RETINOIC ACID

(75) Inventors: Rocco Crimi, Monterotondo (IT); Raniero Cozzi, Monterotondo (IT)

(73) Assignee: Laboratori Farmaceutici Krymi S.p.A., Monterotondo (IT)

( * ) Notice: Subject to any disclaimer, the term of this patent is extended or adjusted under 35 U.S.C. 154(b) by 0 days.

(21) Appl. No.: 13/635,980

(22) PCT Filed: Sep. 9, 2011

(86) PCT No.: PCT/IB2011/053947
§ 371 (c)(1),
(2), (4) Date: Sep. 19, 2012

(87) PCT Pub. No.: WO2012/032493
PCT Pub. Date: Mar. 15, 2012

(65) Prior Publication Data
US 2013/0012582 A1    Jan. 10, 2013

(30) Foreign Application Priority Data
Sep. 10, 2010 (IT) .............................. RM2010A0473

(51) Int. Cl.
| | | |
|---|---|---|
| A61K 8/02 | (2006.01) | |
| A01N 37/00 | (2006.01) | |
| A61K 8/67 | (2006.01) | |
| A61K 8/37 | (2006.01) | |
| A61K 8/81 | (2006.01) | |
| A61Q 19/02 | (2006.01) | |
| A61Q 19/08 | (2006.01) | |

(52) U.S. Cl.
CPC .............. *A61K 8/671* (2013.01); *A61K 8/0212* (2013.01); *A61K 8/375* (2013.01); *A61K 8/8129* (2013.01); *A61Q 19/02* (2013.01); *A61Q 19/08* (2013.01)
USPC .......................................... 424/401; 514/559

(58) Field of Classification Search
USPC .......................................... 424/401; 514/559
See application file for complete search history.

(56) References Cited

U.S. PATENT DOCUMENTS

| | | | | |
|---|---|---|---|---|
| 5,593,680 | A * | 1/1997 | Bara et al. ...................... | 424/401 |
| 5,616,332 | A * | 4/1997 | Herstein ........................ | 424/401 |
| 6,080,390 | A * | 6/2000 | Calello et al. .................. | 424/64 |
| 6,291,519 | B1 | 9/2001 | Kis | |
| 2003/0235553 | A1 * | 12/2003 | Lu et al. ...................... | 424/70.122 |
| 2005/0175641 | A1 | 8/2005 | Deo et al. | |
| 2005/0226899 | A1 * | 10/2005 | Castiglioni et al. ............ | 424/401 |
| 2005/0281851 | A1 * | 12/2005 | Cap ................................ | 424/401 |
| 2007/0243146 | A1 * | 10/2007 | Klock ............................. | 424/59 |
| 2007/0282123 | A1 | 12/2007 | Sato et al. | |
| 2008/0226742 | A1 | 9/2008 | Srinivas et al. | |
| 2009/0203649 | A1 | 8/2009 | Kato et al. | |
| 2011/0144062 | A1 | 6/2011 | Kato et al. | |

FOREIGN PATENT DOCUMENTS

| | | |
|---|---|---|
| CN | 100 379 447 | 4/2008 |
| EP | 0 610 511 | 8/1994 |
| EP | 1 710 225 | 10/2006 |
| JP | 6 293639 | 10/1994 |
| WO | 00/21528 | 4/2000 |
| WO | 2004/010988 | 2/2004 |
| WO | 2006/133131 | 12/2006 |
| WO | 2008/001921 | 1/2008 |

OTHER PUBLICATIONS

INCI Directory. Octyldodecyl Octyldodecanoate [online]. INCI. last updated Feb. 17, 2009 [retrieved on Dec. 12, 2013]. retreived from the internet: <http://www.specialchem4cosmetics.com/services/inci/ingredient.aspx?id=8313>.*
Business Dictonary. Denatured Alcohol. Business Dictionary. avaliable online from: 2007 [retrieved on Dec. 12, 2013] Retrieved from the internet: <http://www.businessdictionary.com/definition/denatured-alcohol.html>.*
International Search Report for PCT/IB2011/053947, five pages (Feb. 2012).
Written Opinion for PCT/IB2011/053947, seven pages (Feb. 2012).
"Water-containing cosmetic mask composition—Containing biological complex of gelatin-glycine-zinc vitamins with vitamin A palmitate, PVA, nipagin, ethanol etc." Derwent abstract XP002283611 (Dec. 1986).

* cited by examiner

*Primary Examiner* — Richard Schnizer
*Assistant Examiner* — Katherine Peebles
(74) *Attorney, Agent, or Firm* — Nixon & Vanderhye PC

(57) ABSTRACT

A formulation for topical use having a filmogenic (peel-off) action for professional and home use, containing high concentrations of Retinoic acid, the method of production and use thereof in the treatment of acne, wrinkles, hyperpigmentations, psoriasis and all imperfections linked to keratinization disorders. The composition also comprises octyldodecyl octyldodecanoate, and polyvinyl alcohol. The composition is in the form of a face mask (pack).

13 Claims, No Drawings

VINYLIC MASK WITH PEEL-OFF EFFECT FOR TOPICAL USE CONTAINING HIGH CONCENTRATIONS OF RETINOIC ACID

This application is the U.S. national phase of International Application No. PCT/IB2011/053947, filed 9 Sep. 2011, which designated the U.S. and claims priority to Italian Application No. RM2010A000473, filed 10 Sep. 2010; the entire contents of each of which are incorporated by reference.

The present invention relates to a composition, preferably in the form of a mask, having a filmogenic action (peel-off effect) for professional and home use, containing retinoic acid (Tretinoin) at a high concentration, to be used in the treatment of acne, wrinkles, hyperpigmentations, psoriasis and all imperfections linked to keratinization disorders. Within the scope of the present invention, by the term retinoic acid (or tretinoin) it is meant both the trans-retinoic acid and the cis-retinoic acid. Retinoic acid, a vitamin A ester present in the cis form and in the trans form with regard to the double bond in position 13, is a yellow crystalline powder, practically insoluble in water, soluble in dichloromethane, moderately soluble in ether, scarcely soluble in ethanol. It is sensitive to air, heat and light, especially in solution. It has the following structural formula, in which the two forms, trans and cis, are not distinct.

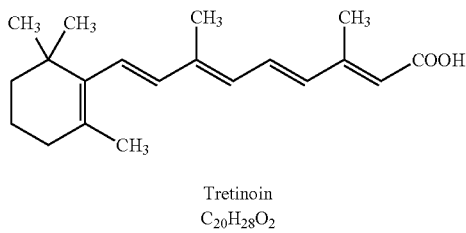 [SMILES: CC1=C(/C=C/C(C)=C/C=C/C(C)=C/C(=O)O)C(C)(C)CCC1]

Tretinoin
$C_{20}H_{28}O_2$

It is known that Trans-Retinoic acid (Tretinoin) is used in preparations for topical use in the treatment of acne vulgaris, comedonal acne and papulo-pustulous acne due to its action normalizing the keratinization of the acroinfundibulum and promoting comedolysis. Moreover, it is known that retinoic acid exhibits various biological actions, finalized to the treatment of photoaging, inducing an increase of keratinocyte turnover, neoangiogenesis and neosynthesis of collagen fibers (type 1 procollagen). In particular, Tretinoin proved capable of inducing, with a dose-dependent mechanism, a clinical improvement and reduction or regression of histological alterations typical of photoaging (Kligman L:H.: Prevention and repair of photoaging: sunscreens and retinoids. Cutis, 43: 458-465, 1989—Torras H.: Retinoids in aging. Clin Dermatol, 14: 207-215, 1996.). After 3-6 months of therapy with Tretinoin, clinical improvement is observed for skin texture and laxity, for wrinkledness, for skin dyschromias. Moreover, topical administration of Trans-Retinoic acid for at least 6 months induces partial reduction of microscopic alterations, with thinning of epidermal hyperkeratosis, with a more compact setting of the corneal layer, increase of the granulous layer, loss of cellular atypia and restoration of keratinocyte polarity, reduction of basal layer pigmentation with a more uniform melanosome distribution and, in the derm, no deposit of collagen fibers. One of the demonstrated mechanisms for the treatment and prevention of photoinduced aging consists in the inhibition of the synthesis of metalloproteinases which degrade the dermal extracellular matrix. UVB rays, by kinase activation, stimulate expression of c-jun and c-fos proto-oncogens, which, by binding into a protein complex, are in turn capable of activating the nuclear transcription factor AP-1 with gene expression in fibroblasts of collagenase (MMP-1), of gelatinase B (MMP-9) and of stromelysin (MMP-3), proteinases which degrade the extracellular matrix. Tretinoin, by inhibiting AP-1 formation, reduces UVB-induced damages on the dermal extracellular matrix.

To date, several Trans-Retinoic acid-based products are available, with concentrations of said acid ranging from 0.02 to 0.3% b/w. The reason for these low values lies in the fact that one among the main drawbacks of retinoic acid, in addition to its toxicity and irritating action, is just the difficulty to be introduced at high concentrations and homogeneously into products stable over time. Physical stability of compositions containing retinoic acid is difficult to control, owing to the tendency of the acid to precipitate, even in the short run, in a microcrystalline form.

The present invention proposes to provide improved retinoic acid-based compositions overcoming the drawbacks of state of the art compositions. According to the invention, there are obtained compositions with concentrations of up to 8% by weight (b/w) of retinoic acid, with a preferred value of 5%, and a particularly preferred value of 2.5%, advantageously in the form of a mask with peel-off effect, in which moreover retinoic acid concentration is homogeneous and stable over time and the acid does not cause skin toxicity. The mask is however pleasant to use and does not cause any irritating effect by local application on the skin.

Objects of the present invention are the composition of which at independent claim 1 and the method of which at independent claim 10; further objects are set forth in the dependent claims thereof. The composition according to the present invention advantageously finds therapeutic or cosmetic use in the form of a mask. By the term "mask", within the scope of the present invention, is to be understood the composition of the invention formed according to the needs of the specific site of application on the body, such as face, neckline, etc. The composition of the invention entails several advantages compared to other forms of administration, such as:

- great ease of control and application on skin parts to be treated;
- absence of toxicity due to the presence of polyvinyl alcohol, which is capable of creating a surface barrier preventing retinoic acid absorption in the period of application, eliminating all potential risks of toxicity related thereto.
- absence of skin irritation, thanks to the time-dose ratio allowing to administer a high dose of Tretinoin over a limited time (about 20 minutes)

According to the invention, the stability of Trans-Retinoic or 13-Cis acid at high concentrations is obtained by the presence in the formula of Octyldodecyl Octyldodecanoate (BIOSIL BASIC C-38), highly branched GUEBERT ester, obtained from a Guebert alcohol and a Guebert acid. Thanks to its chemical structure, it possesses an interesting stability profile. Like other esters, it is insoluble in water but soluble in Isopropanol and Cyclomethicone. Preferably, the weight ratio between Trans-retinoic or 13-Cis acid and Octyldodecyl Octyldodecanoate (BIOSIL BASIC C-38), should be comprised between 1:4 and 1:8.

The gelling agent allowing to obtain the desired viscosity is polyvinyl alcohol, whose concentration by weight is comprised between 5% and 15%.

The method of production of the composition subject-matter of the present invention is the following. In a suitable vessel, Disodium EDTA, Acrylates/C10-30 Alkyl Acrylate Crosspolymer, Polyvinyl Alcohol, Propylene Glycol are pre-arranged in production water heated to 70° C. In a separate vessel, Otyldodecyl Octyldodecanoate (BIOSIL BASIC C-38) is preheated to 40° C., then Retinoic or 13-Cis acid is added and homogenized by a turbine having a controlled speed. At the end of this step the compound obtained is added to the preceding phase, carrying on a slow and constant stirring. Finally, salicylic acid pre-solubilized in denatured ethyl alcohol and Imidazolidinyl urea pre-dissolved in a small amount of deionized water are added. At the end of the steps the compound is left under constant stirring until desired viscosity is achieved.

The composition according to the invention, preferably in the form of a vinilyc mask thus obtained, is intended for:
1) fight against skin ageing, be it photoinduced or not photoinduced, to reduce pigmentations or actinic keratoses, wrinkles, striae distensae;
2) treatment of dermatological affections linked to a keratinization disorder (acne in its different forms, ichthyoses, psoriases, dermatitises, xeroses;
3) treatment of dermal or epidermal proliferations (warts);
4) treatment of dermatoses or blisters.

The treatment consists in the uniform application of the mask, with a circular center-to-outside motion, said mask to be left in place to dry for about 30 min. As soon as it is dry, the mask should be uniformly removed with a top-to-bottom motion, with the aid, at the end of the step, of a cotton disk soaked with suitable detergent oil in order to accurately remove any trace of the mask. The treatment is to be repeated weekly for at least 4-5 weeks, thereafter a maintenance session every 30-40 days is advisable. An example of composition of vinylic mask according to the invention will now be given, by way of illustration and without any limitative purpose:

| N° | Ingredient | Amount in 100 g of gel |
|---|---|---|
| 1 | Water | 57.37 g |
| 2 | Disodium EDTA | 0.07 g |
| 3 | Imidazolidinyl Urea | 0.20 g |
| 4 | Acrylates/C10-30 Alkyl Acrylate Crosspolymer | 0.53 g |
| 5 | Polyvinyl Alcohol | 10.00 g |
| 6 | Propylene Glycol | 3.33 g |
| 7 | Retinoic acid (Tretinoin) | 2.50 g |
| 8 | Octyldodecyl Octyldodecanoate (BIOSIL BASIC C-38) | 10.00 g |
| 9 | Denatured Alcohol | 16.00 g |
| 10 | Salicylic Acid | 0.80 g |

The mask has the following chemico/physical reference characteristics:

| | |
|---|---|
| pH comprised in the range | 3.5-4.5 |
| viscosity comprised between | 15.000-23.000 mpa |
| density comprised between | 0.97 ml-1.01 ml |
| Retinoic acid titer in 100 g of gel | 2.25 g-2.75 g |

Tests carried out on this mask—and reported hereinafter—highlighted the following properties:
1) absence of skin permeation of retinoic acid during the application period
2) absence of skin irritation.
3) absence of direct contact cytotoxicity.
4) absence of allergic sensibilization

EXAMPLE 1

Assessing the Absence of Skin Permeation of Retinoic Acid During the Application Period by Ex Vivo Determination of Skin-Accumulated Amount of the Tretinoin Contained in the Polyvinylic Mask An ex vivo study of the skin-accumulated amount of retinoic acid contained in the polyvinylic mask was conducted at the Department of Pharmaceutical Sciences of the University of Milan. The aim of the work was the assessment of the barrier effect by polyvinyl alcohol toward the percutaneous absorption of Trans-Retinoic acid under standard conditions of use of the mask. A sample of polyvinylic mask containing 2.5% Trans-Retinoic acid (Lot n° P10044) was subjected to the test. The membrane was prepared by using skin of human origin, which is the most appropriate for foreseeing in vivo absorption. As it is known that the skin barrier against permeation of exogenous substances by passive diffusion mainly consists of the corneal layer, absorption was assessed by using as membrane the corneal endothelial layer (SCE) obtained by mechanical separation of the derm from the skin.

Results—Preliminary analyses were conducted which demonstrated that the compositions examined did not contain products capable of interfering on quantitative determination of retinoic acid. The difference in the amounts of tretinoin accumulated in the membranes over the two exposure times, reported in the following table 1, is not significant; therefore, it is evident how the barrier formed by polyvinyl alcohol interferes, by inhibiting percutaneous absorption of Trans-Retinoic acid and therefore its undesired systemic effects, which instead are present in products lacking said barrier and containing it.

TABLE 1

Amount of SCE-accumulated tretinoin, expressed as $\mu g/cm^2$ and % w/w with respect to the amount applied (n = 3, average ± s.d.).

| | Exposure time | |
|---|---|---|
| | 30 min | 60 min |
| Tretinoin ($\mu g/cm^2$) | 1.32 ± 1.01 | 1.63 ± 0.23 |
| Tretinoin (% w/w) | 1.15 ± 0.84 | 1.38 ± 0.12 |

EXAMPLE 2

Absence of Skin Irritation on the Polyvinylic Mask

On the product being examined, a "polyvinylic mask" manufactured according to modes and percentages described in the invention, a toxicological study was conducted in order to provide data needed for assessment of local toxicity at the skin level, by the skin irritation assay according to EN ISO 10993-10:2002

The polyvinylic mask (Lot Nr. 090709 G) was applied as such on intact skin of 3 albino rabbits for a time period of 4 hours. At the end of the detections, a primary irritation index equal to 0.11 was found. Reactions were observed 1 h after gauze removal, and again 24, 48 and 72 hours after exposure. On the basis of the results obtained, interpreted according to what is provided for by EN ISO 10993-10:2002, the product must be deemed as non-irritating for the skin.

EXAMPLE 3

Cytotoxicity Assessment

On the product being examined, a "polyvinylic mask" manufactured according to modes and percentages described in the invention, a cytotoxic effect assessment was conducted, by cytotoxicity assay on agar according to EN ISO 10993-5:2009. The cytotoxicity test was performed by using a confluent culture of BalbC 3T3 cells in the exponential phase of growth. After 24 h of incubation, cell culture was observed in order to assess biological reactivities. The results highlight that, in the wells treated with the product being examined, the detected degree of reactivity of the limited area below the substance being examined was no higher than 2. On the basis of the results obtained, interpreted according to what is provided for by EN ISO 10993-5:2009, the product being examined should be deemed as non-cytotoxic.

EXAMPLE 4

Delayed Hypersensitivity Test

On the product being examined, a "polyvinylic mask" manufactured according to modes and percentages described in the invention, a toxicologic study was conducted in order to provide data needed for assessment of local toxicity at the skin level, by assay with the Guinea pig maximization test according to EN ISO 10993-10:2002. For the above-mentioned assay 15 Guinea pigs were used, of which 10 treated with the product being examined and 5 used as control. The delayed hypersensitivity assay consists of an inducing phase and a triggering phase. After 48 h and 72 h from the start of the triggering phase, reactions of treated and control animals were assessed. Nothing abnormal was detected in treated animals and in controls. On the basis of the results obtained, interpreted according to what provided for by EN ISO 10993-10:2002, the product must be defined as non-sensibilizing.

Also the following chemico-physical determination was carried out.

EXAMPLE 5

Determination of Stability and Uniformity of Concentration of Trans-Retinoic Acid in the Polyvinylic Mask A comparative study for the determination, stability and uniformity of concentration of Trans-Retinoic acid in the polyvinylic mask was conducted, by chromatography, at the Department of Pharmacological Sciences of the University of Studies of Milan. Two lots of polyvinylic mask were analyzed, containing the same concentration of Trans-Retinoic acid (2.5%) solubilized in different esters, respectively Octyldodecyl Octyldodecanoate (BIOSIL BASIC C-38) for lot N° P10044 (invention) and Peg-7 Glyceril Cocoate (CETIOL HE SPECIAL) for lot N° 120209 (comparison). Preliminary analyses were conducted, which demonstrated that the compositions examined did not contain products capable of interfering in the quantitative determination of retinoic acid. Hereinafter, the methodology used is described: quantitative analysis of Trans-Retinoic acid is performed by HPLC (HP1100, Chemstations Hewlett Packard, USA).

Operating Conditions:

Reversed-phase column: C18 LiChrospher 100 RP-18E, 125×4.0 mm, 5 µm. Mobile phase: solution of 81 volumes of ethanol and 19 of phosphate buffer (25 mM, pH 2.5), kept at a temperature of 40° C. The mobile phase was degassed and filtered before use. Flow: 1 ml/min. Detector: UV-VIS adjusted to 353 nm. Injection volume: 20 µm. Retention time: 13.5 min. For calibration, standard solutions of tretinoin in the mobile phase, in the concentration range of 0.2-20 µg/ml, were used.

For each batch record, samplings were performed with the following modes:

sampling 1: without mixing, from a superficial point of the bulk;

sampling 2: without mixing, from a point internal to the bulk;

sampling 3: after homogeneous stirring.

RESULTS: Experimentally determined content of Trans-Retinoic acid in the polyvinylic mask identified by Lot 120209 (control) was found to be comprised between 4.1 and 1.9%±0.1% w/w relative to the collection site, whereas the producer had declared a homogeneous content equal to 2.5%. Trans-Retinoic acid content, experimentally determined in Lot P10044 according to the invention, was found to be equal to 2.4±0.1% w/w, in compliance to what had been declared by the producer, equal to 2.5% in all collection sites. The foregoing demonstrates the scarce homogeneity of the control product, making its application difficult just due to the variability of the composition; the latter tends to randomly split into zones with different concentrations, making a correct application of the mask impossible just due to the retinoic acid toxicity problems highlighted in the foregoing. On the contrary, the mask according to the invention has homogeneity of concentration allowing a safer, easier and more effective application thereof. Moreover, as highlighted in the following table, retinoic acid concentration of the mask according to the invention remains constant for 24 months (shelf life), whereas that of the control product decreases rapidly, as may be highlighted in the following Tables 2 and 3, reporting long-term stability tests of compositions according to the invention (Table 2) and compositions according to the state of the art (Table 3). A comparative analysis of the results highlights how the compositions according to the state of the art do not meet the specifications already after one year of storage, whereas the compositions according to the invention meet the specifications up to 24 months (each passage between successive Ts denotes a 6-month difference). It can be concluded that the use of Octyldodecyl Octyldodecanoate (compositions of Table 2) unlike other esters makes the concentration of Trans-Retinoic acid in the polyvinylic mask stable and homogeneous even at high concentrations and with long shelf lives.

TABLE 2

| Accelerated stability Lot P10044 | MONTHS | | | | | |
|---|---|---|---|---|---|---|
| (invention) | T0 | T1 | T2 | T3 | T6 | SPECIFICATIONS |
| Retinoic acid titer (sampling 1) | 2.42 | 2.40 | * | 2.31 | 2.43 | 2.25-2.75% |
| Retinoic acid titer (sampling 2) | 2.40 | 2.38 | * | 2.38 | 2.39 | |
| Retinoic acid titer (sampling 3) | 2.45 | 2.43 | * | 2.40 | 2.42 | |

TABLE 3

| Accelerated stability Lot 120209 (control) | MONTHS | | | | | SPECIFICATIONS |
|---|---|---|---|---|---|---|
| | T0 | T1 | T2 | T3 | T6 | |
| Retinoic acid titer (sampling 1) | 4.21 | 1.90 | x | x | x | 2.25-2.75% |
| Retinoic acid titer (sampling 2) | 2.10 | 2.75 | x | x | x | |
| Retinoic acid titer (sampling 3) | 3.22 | 3.99 | x | x | x | |

Legend:
T = corresponds to 6 months; long-term stability and therefore an overall period of 24 months, T0 to T6
Specifications = acceptability range of retinoic acid concentration in the product
Sampling 1 = bulk surface
Sampling 2 = bulk inside
Sampling 3 = after homogeneous stirring
x = product found outside specifications
* = in this case it was not necessary to carry out tests at time T2 (12 months) but they were carried out directly at time T3 (18 months) and T6 (24 months).

The invention claimed is:

1. A composition comprising retinoic acid and polyvinyl alcohol, characterized in that it contains 1-8% by weight of retinoic acid and 8-15% by weight of octyldodecyl octyldodecanoate with reference to the total weight of the composition.

2. The composition according to claim 1, wherein the octyldodecyl octyldodecanoate is present in a weight ratio comprised between 4:1 and 8:1 with respect to the concentration by weight of the retinoic acid.

3. The composition according to claim 1, wherein the polyvinyl alcohol is contained in a ratio comprised between 5 and 15% by weight with reference to the total weight of the composition.

4. The composition according to claim 1, further comprising denatured ethyl alcohol in a ratio of between 10 and 30% by weight with reference to the total weight of the composition.

5. The composition according to claim 1, further comprising additives selected from the group consisting of disodium EDTA, imidazolidinyl urea, acrylates/C10-30 alkyl acrylate crosspolymer, propylene glycol, and salicylic acid.

6. The composition according to claim 1, in the form of a mask.

7. A method of using the composition according to claim 1, comprising applying the composition to skin in cosmetic treatment of acne, wrinkles, hyperpigmentations, psoriasis or keratinization disorders.

8. A method of production of a composition comprising:
 a. combining in a vessel polyvinyl alcohol, disodium EDTA, acrylates/C10-30 alkyl acrylate crosspolymer, and propylene glycol in production water at a temperature comprised between 60 and 80° C.;
 b. preheating, in a separate vessel, 8-15% by weight of octyldodecyl octyldodecanoate with reference to the total weight of the composition to 40° C., to which 1-8% by weight of retinoic or 13-cis retinoic acid with reference to the total weight of the composition is added and homogenized with a turbine having a controlled speed;
 c. adding the mixture of step b) to the vessel of step a) with stirring;
 d. adding to the mixture of step c) salicylic acid pre-solubilized in denatured ethyl alcohol and imidazolidinyl urea pre-dissolved in deionized water; and
 e. constant stirring of the mixture of step d) until reaching a viscosity comprised between 15,000 and 23,000 mpa.

9. The composition according to claim 1, wherein the composition has (i) viscosity comprised between 15,000 and 23,000 mpa and (ii) pH comprised between 3 and 5.

10. A composition comprising 1-8% by weight of retinoic acid, 8-15% by weight of octyldodecyl octyldodecanoate, 5-15% by weight of polyvinyl alcohol, and 10-30% by weight of denatured ethyl alcohol with reference to the total weight of the composition.

11. The composition according to claim 10, wherein the octyldodecyl octyldodecanoate is present in a weight ratio comprised between 4:1 and 8:1 with respect to the concentration by weight of the retinoic acid.

12. The composition according to claim 10, wherein the composition has (i) viscosity comprised between 15,000 and 23,000 mpa and (ii) pH comprised between 3 and 5.

13. A method of using the composition according to claim 10, comprising applying the composition to skin in cosmetic treatment of acne, wrinkles, hyperpigmentations, psoriasis or keratinization disorders.

* * * * *